(12) United States Patent
Winterbottom et al.

(10) Patent No.: US 6,746,454 B2
(45) Date of Patent: Jun. 8, 2004

(54) IMPLANT INSERTION TOOL

(75) Inventors: John M. Winterbottom, Jackson, NJ (US); Erik O. Martz, Howell, NJ (US)

(73) Assignee: Osteotech, Inc., Eatontown, NJ (US)

( * ) Notice: Subject to any disclaimer, the term of this patent is extended or adjusted under 35 U.S.C. 154(b) by 0 days.

(21) Appl. No.: 10/046,866

(22) Filed: Jan. 15, 2002

(65) Prior Publication Data

US 2002/0058950 A1 May 16, 2002

Related U.S. Application Data

(60) Provisional application No. 60/264,601, filed on Jan. 26, 2001, and provisional application No. 60/246,297, filed on Nov. 7, 2000.

(51) Int. Cl.[7] ............................................. A61B 17/58
(52) U.S. Cl. ....................................... 606/99; 294/99.2
(58) Field of Search ........................... 606/61, 49, 99, 606/210, 211, 198, 191; 623/17.11, 17.12, 17.13, 17.14, 17.15, 17.16; 600/201, 214, 215, 218, 219, 220; 294/99.2; D28/55

(56) References Cited

U.S. PATENT DOCUMENTS

| | | | | |
|---|---|---|---|---|
| 1,133,334 A | * | 3/1915 | Strycker | 269/6 |
| 1,174,004 A | * | 2/1916 | Greenwald | 294/99.2 |
| 1,886,127 A | * | 11/1932 | Silvis | 606/210 |
| 2,042,985 A | * | 6/1936 | Gardella | 606/210 |
| 3,253,327 A | * | 5/1966 | McElligatt | 29/741 |
| 4,442,837 A | * | 4/1984 | Keatley | 606/131 |
| 4,736,738 A | | 4/1988 | Lipovsek et al. | |
| 4,878,915 A | | 11/1989 | Brantigan | |
| 4,917,677 A | * | 4/1990 | McCarthy | 606/151 |
| 5,192,327 A | | 3/1993 | Brantigan | |
| 5,385,471 A | * | 1/1995 | Chuen | 433/153 |
| 5,443,514 A | | 8/1995 | Steffee | |
| 5,449,374 A | * | 9/1995 | Dunn et al. | 606/208 |
| 5,520,704 A | * | 5/1996 | Castro et al. | 606/208 |
| 5,522,899 A | | 6/1996 | Michelson | |
| 5,653,762 A | | 8/1997 | Pisharodi | |
| 5,716,415 A | | 2/1998 | Steffee | |
| 5,720,751 A | | 2/1998 | Jackson | |
| 5,741,253 A | | 4/1998 | Michelson | |

(List continued on next page.)

FOREIGN PATENT DOCUMENTS

| | | |
|---|---|---|
| FR | 985 188 A | 7/1951 |
| WO | WO 97 3006 A | 8/1997 |
| WO | WO 00/24327 | 5/2000 |

OTHER PUBLICATIONS

Freebody, M.B., B.S., F.R.C.S. (Ed.), Douglas, *Anterior Interbody Fusion for Spondylolisthesis (Via Transperitoneal Approach*, source unknown.

Peer, M.D., Lyndon A., *Transplantation of Tissues, Cartilage, Bone, Fascia, Tendon and Muscle*, The Williams & Wilkins Company, Baltimore, 1944, pp. 227–236.

Cauthen, M.D., F.A.C.S., Joseph C., *Lumbar Spine Surgery*, 2d Ed., Williams & Wilkins, Baltimore, 1988, pp. 228–247.

Primary Examiner—Michael J. Milano
Assistant Examiner—D. Jacob Davis
(74) Attorney, Agent, or Firm—Carella Byrne Bain Gilfillan Cecchi et al.; Elliot M. Olstein; William Squire

(57) ABSTRACT

A spinal implant tool comprises a steel shaft bifurcated into shaft portions at one end at which a pair of extensions extend from the bifurcated shaft portions. The extensions are flat members which extend from an implant impact element at the end of each of the shaft portions. A spinal bone implant is inserted between the extensions. A shaft portion displacement member has a stud threaded to one of the shaft portions and a knob head for capturing the other shaft portion to the member threaded stud. When the knob is rotated the shaft members are moved apart or closer together. A stop member limits the spread apart distance of the shaft portions.

13 Claims, 3 Drawing Sheets

U.S. PATENT DOCUMENTS

| | | |
|---|---|---|
| 5,782,830 A | 7/1998 | Farris |
| 5,885,299 A | 3/1999 | Winslow et al. |
| 5,885,300 A | 3/1999 | Tokuhashi et al. |
| 5,893,853 A * | 4/1999 | Arnold ..................... 606/133 |
| 5,910,141 A | 6/1999 | Morrison et al. |
| 6,004,326 A | 12/1999 | Castro et al. |
| 6,033,405 A | 3/2000 | Winslow et al. |
| 6,033,438 A | 3/2000 | Bianchi et al. |
| 6,042,582 A | 3/2000 | Ray |
| 6,063,088 A | 5/2000 | Winslow |
| 6,174,311 B1 | 1/2001 | Branch et al. |
| 6,206,922 B1 * | 3/2001 | Zdeblick et al. ......... 623/17.11 |
| 6,248,123 B1 * | 6/2001 | McDonald .................. 606/210 |
| 6,267,763 B1 * | 7/2001 | Castro ......................... 606/61 |
| 6,440,142 B1 * | 8/2002 | Ralph et al. .................. 606/99 |

\* cited by examiner

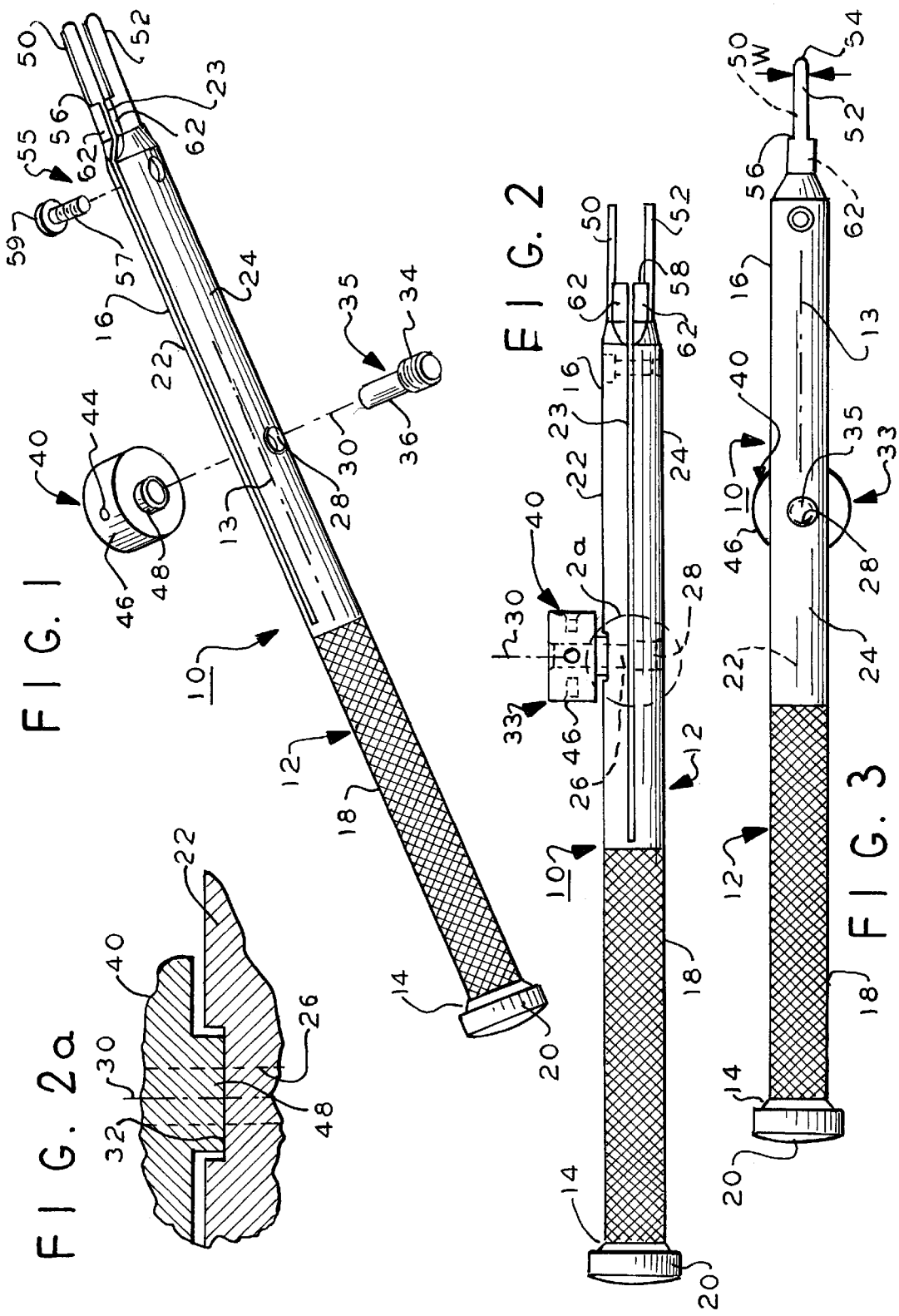

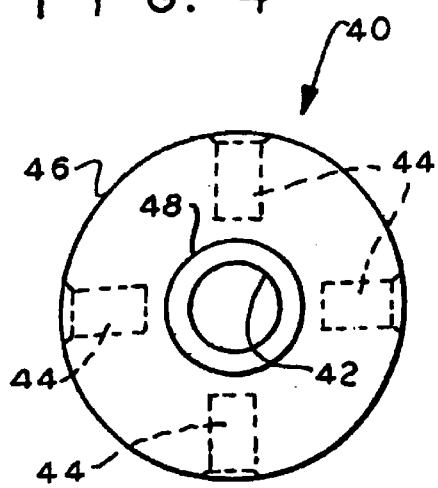
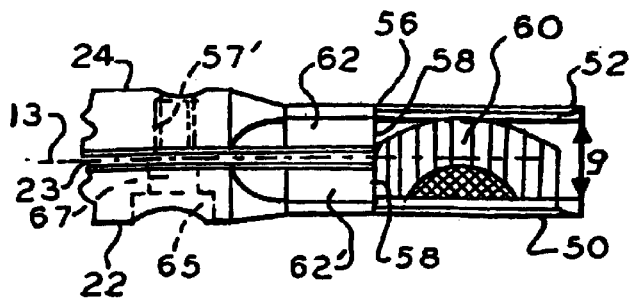
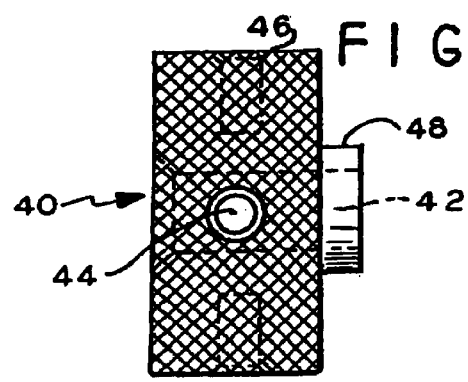
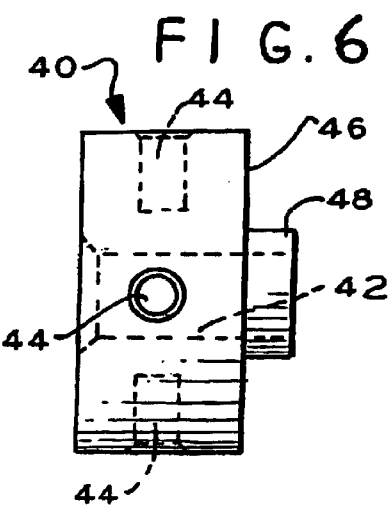
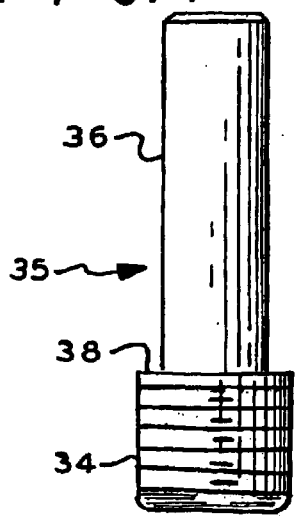
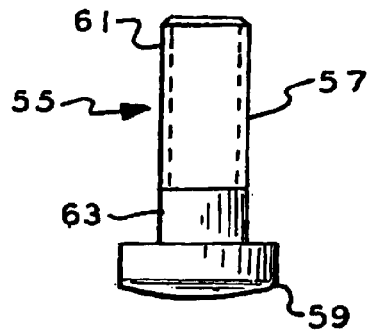

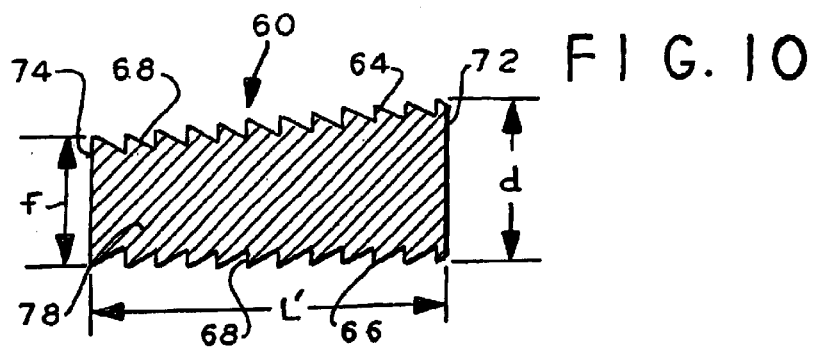
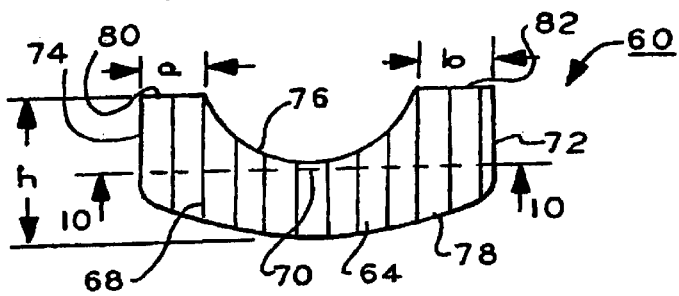 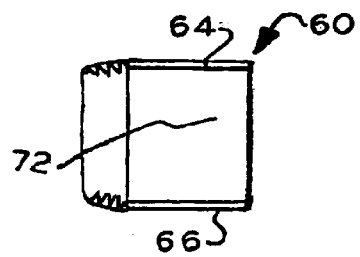
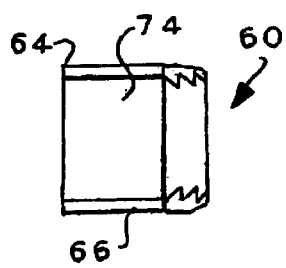 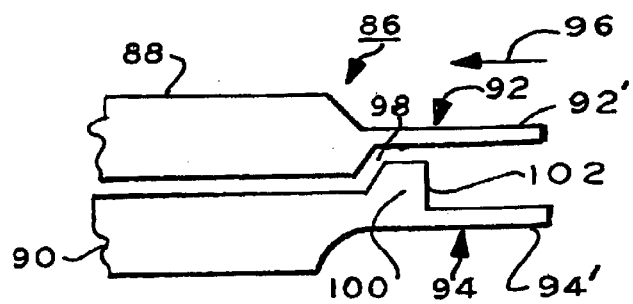
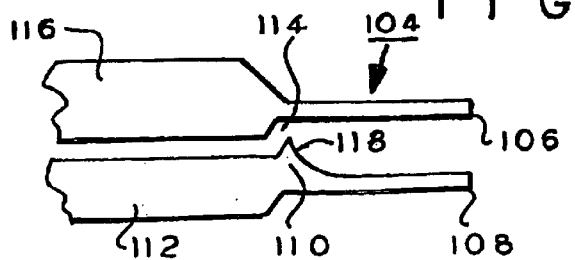

IMPLANT INSERTION TOOL

THIS APPLICATION CLAIMS BENEFIT OF PROVISIONAL APPLICATION SERIAL No. 60/264,601 FILED Jan. 24, 2001, and claims benefit of 60/246,297 filed Nov. 11, 2000.

This invention relates to implant insertion tools, and more particularly, to spinal implant insertion devices for insertion of implants into the intervertebral disc space.

Of interest are commonly owned copending application Ser. No. 09/705,377 entitled Spinal Intervertabral Implant filed May 3, 2000 in the name of Lawrence Shimp et al. and No. 60/246,297 entitled Spinal Intervertebral Implant Insertion Tool filed Nov. 7, 2000 in the name of Erik Martz et al. incorporated by reference herein.

Spinal implants, sometime referred to as grafts, are in wide use and typically comprise non-bone physilogically compatible metal or other non-bone materials or bone. Reference is made to the aforementioned copending application Ser. No. 09/705,377 for a bone implant. A similar type of implant disclosed therein is described herein in connection with FIGS. 10–13. What is desired is an implant insertion tool or device that is convenient to use, permits the surgeon to easily access the implant disc site in the patient and insert the implant in the desired orientation. The prior art is replete with implant insertion tools and devices.

For example, U.S. Pat. No. 5,782,830 to Farris discloses an implant insertion device. The device includes a handle, a shaft having a proximal end attached to the handle, and a distal end. A pair of jaws each having a first end is attached to the distal shaft end and a free second end. A gripping element is at the second end. The free ends of the jaws are movable between gripping positions to grasp the implant between the gripping elements and release positions to release the implant. The jaws are biased apart to the release positions. Each gripping element defines a substantially uniform or flat gripping surface that include teeth. A hollow sleeve is slidably disposed over the jaws for forcing the jaws together toward the gripping position.

U.S. Pat. No. 5,385,471 discloses a dental instrument comprising a grasping device in the form of a tweezer member having a finger receiving ring detachably connected to one of the legs of the tweezer member. The instrument is used to hold and insert a Cerec inlay in a tooth undergoing restoration.

U.S. Pat. No. 3,844,291 discloses a grip device in the form of a spring tubular pocket size device to grip and hold small things. The device includes a tubular body, a sleeve with a handle portion, a latch for supporting a spring and a cap or second handle member. Spring jaws are normally biased apart. A push rod is retracted and cam surfaces on a guide means urges the jaws inwardly to grip an object.

U.S. Pat. No. 4,877,020 to Vich discloses an apparatus for inserting a cylindrical externally threaded bone graft The instrument has an elongated handle, and a control rod extends axially through the handle and rotatably and threadably attached thereto. The control rod has a part which projects therefrom and releasably grips the implant.

U.S. Pat. No. 5,910,141 discloses a rod introduction apparatus for approximating a longitudinal member and an implant to permit fixation therebetween.

U.S. Pat. No. 5,946,988 discloses a tool for driving pedicle screws. The tool has clamping jaws secured to a shaft and a lateral projection tiltably received by one of the jaws. The tool has an axially slidable actuating member guided on the shaft.

U.S. Pat. No. 6,053,933 discloses a gripping unit for application in minimally invasive surgery. A stationary jaw is rigidly attached to a base section. A movable jaw is connected via a joint to a push/pull rod and an operating handle. The stationary jaw, the movable jaw, the rod and the base section have in the longitudinal direction a channel to receive additional instruments wherein the base section and rod form a circular conduit.

U.S. Pat. No. 6,099,483 discloses a jaw assembly for an endoscopic instrument. which includes first and second end effectors, a screw, and optionally a washer. The end effectors have arms biased apart. The screw has a threaded portion engaging the distal end of the instrument and a head portion with a pair of arm receiving grooves. The arms are captured between the screw and washer. The grooves are provided with upstanding pins which engage mounting holes in the arms.

U.S. Pat. No. 6,099,550 discloses a surgical instrument having jaws biased apart and an operating channel and method for use thereof. The instrument includes a forceps unit for positioning within an anatomical cavity. The forceps unit has a housing, an outer tubular member, an intermediate tubular member and a handle mechanism for creating relative movement between the intermediate and outer tubular members. The outer tubular member has a proximal end mounted by the housing and terminates distally at a distal end. The intermediate member has a tubular body disposed telescopically within the outer member. Relative movement of the outer tubular member over the jaws causes the jaws to close.

U.S. Pat. No. 6,174,311B1 discloses an interbody fusion grafts and instrumentation. Implants similar to the implant described herein are disclosed and instrumentation for insertion of such implants are also disclosed. One implant holder includes a handle, a gripping head a first branch and a second brand pivotally attached to the first branch with a pivot pin. The gripping head includes a first gripping arm integral to the second branch and a second gripping arm integral to the second branch. A recess cavity is formed between opposing gripping arms. The gripping arms include projections which matingly engage first and second indents on the implant. The gripping head includes a surface for contacting the tool engaging end of the implant to drive the implant into a preformed cavity. The gripping arms include impacting surfaces. One gripping arm remains stationary and the other pivots about the pivot pin. A locking pin prevents pivoting of the second branch. the implant is released by disengaging the locking pin. The implant is C-shaped or J-shaped for implantation in the intervertebral disc space.

A second embodiment of a implant holder tool is also disclosed. It has a gripping head and a handle for releasably securing and impacting the implant duirng insertion. The gripping head includes a roughened impacting surface orthogonal to the insertion direction. The gripping head includes a first surface orthogonal to the impacting direction and a second surface inclined to the impacting direction. In addition a shaft extension secures the implant to the gripping head.

U.S. Pat. Nos. 5,797,909, 6,083,225, 6,080,155 and 6,096,038 disclose still other instrumentation for inserting spinal implants.

An implant insertion tool according to the present invention comprises an elongated shaft having a longitudinal axis and proximal and distal ends, the shaft having a bifurcated distal end forming first and second shaft portions arranged to flex toward and away from each other in a direction generally normal to the axis. A handle is at the proximal shaft end and an implant gripping extension extends from each the shaft portion in a distal direction for gripping an implant therebetween. A displacement member is attached to the shaft portions for displacing the first and second portions relative to each other in the generally normal directions toward and away from each other. A stop member is secured to the portions for limiting the maximum distance the shaft portions and extensions can separate.

In one aspect, the displacement member comprises a threaded stud, a smooth surface circular cylindrical shank attached to the stud and a knob attached to the shank distal the stud, the shank for rotatable attachment to the first shaft portion and the stud for threaded engagement with the second shaft portion, the shank, knob and stud being dimensioned to capture the second portion between the stud and the knob.

In a further aspect, the stop member comprises a shank and a head attached to the shank, the end of the shank distal the head being threaded to one of the shaft first and second portions and the head engaged with the other of the shaft first and second portions, the head being larger than the shank for capturing the other of the shaft first and second portions thereto.

In a further aspect, the normal quiescent position of the extensions is arranged to receive the implant therebetween such that rotation of the knob closes the spacing between the extensions to grip the implant.

Preferably the stud has a diameter greater than that of the shank.

In a further aspect, the displacement member comprises a threaded stud attached to the first shaft portion, a shank attached to and passing through the second shaft portion and a knob attached to the shank, the knob, shank and stud being arranged to capture the second member to the shank.

In a further aspect, the tool according to the present invention comprises an elongated shaft having a longitudinal axis and proximal and distal ends, the shaft having a bifurcated distal end forming first and second shaft portions arranged to flex toward and away from each other in a direction generally normal to the axis. A handle is at the proximal shaft end. An implant gripping extension extends from each shaft portion in a distal direction for gripping an implant therebetween. A displacement member is attached to the shaft portions for displacing the first and second shaft portions relative to each other in the generally normal direction toward and away from each other, the displacement member comprising movable displacement means having first and second positions for forcing the shaft portions apart in the first position for receiving and releasing the implant and for forcing the shaft portions together to an implant gripping state in the second position.

IN THE DRAWING

FIG. 1 is an isometric exploded view of an implant insertion tool according to the present invention;

FIG. 2 is a top plan view of the assembled assembly of FIG. 1;

FIG. 2*a* is a more detailed view of a portion of the assembly of FIG. 2 taken at region 2*a*;

FIG. 3 is a side elevation view of the assembly of FIG. 2;

FIG. 4 is a plan view of the knob of the assembly of FIG. 1;

FIGS. 5 and 6 are respective side elevation views of the know of FIG. 4 with and without knurling respectively on the external surface of the knob;

FIG. 7 is a side elevation view of a stud member which is attached to the knob of FIG. 1;

FIG. 8 is a side elevation view of a stop member employed in the embodiment of FIG. 1;

FIG. 9 is a top plan view of the implant holding jaws of the assembly of FIG. 2 with the implant held by the jaws;

FIGS. 10–13 are various views of the implant of FIG. 9 wherein FIG. 10 is a sectional view taken along lines 10—10 of FIG. 11, FIG. 11 is a top plan view of the implant for use with the tool of FIG. 1, and FIGS. 12 and 13 are respective end views of the implant of FIG. 11; and FIGS. 14*a* and 14*b* are fragmented schematic side elevation views of the extension ends of the shaft portions of tools according to further embodiments of the present invention.

In FIGS. 1, 2 and 3, implant insertion assembly 10 comprises an elongated shaft 12 defining longitudinal axis 13 and having a proximal end 14 and a distal end 16. The proximal end 14 comprises a solid metal preferably stainless steel handle 18 having a knurled or roughened gripping surface. The proximal end of the handle 18 is formed into an enlarged disc-like grip member 20. Approximately medially the shaft 12 and extending toward the distal end 16 is a bifurcated portion comprising bifurcated shaft portions 22 and 24. Shaft portions 22 and 24 form a gap 23 therebetween.

The shaft portion 22 has a through bore 26. The shaft portion 24 has a threaded bore 28 aligned with bore 26 on axis 30. The threaded bore 28 has a larger diameter than bore 26, which is a smooth surface circular cylindrical bore. A circular recess 32, FIG. 2*a*, is formed in a surface of the shaft portion 22 aligned on axis 30 and concentric therewith as are bores 26 and 28.

A displacement member 33 includes a shank portion 35 and a knob 40. Shank portion 35 comprises a threaded stud 34 is attached to a smooth walled circular cylindrical shank 36, FIGS. 1 and 7, as a one piece metal element which may also be stainless steel. The stud 34 is larger in diameter than shank 36. Shank 36 is rotatably and slidably mounted in shaft portion 22 bore 26 and can axially displace in this bore along axis 30. The stud 34 is threaded to bore 28. The threaded stud 34 has a shoulder 38 at the shank 36. This shoulder abuts the shaft portion 22 in the gap 23. The gap 23 may be about 0.060 inches.

Knob 40 is attached to the shank 36 by welding or other fixed securing arrangement after the shank 36 is attached to shaft portion 22 and the stud 34 is engaged in bore 28. The shoulder 38 of the shank portion 35 is located in the gap 23 at the time the shank 36 is attached to the knob. The shank 36 is received in bore 42 of the knob 40. The knob 40 and shank portion 35 when fixed then rotate as a unit when the knob 40 is rotated.

The knob 40 has a plurality of blind bores 44 at right angles to bore 42. The knob 40 has a finger gripping head 46 and a right circular cylindrical boss 48. The boss 48 engages the recess 32 in the shank portion 22. The portion 22 is captured between the knob boss 48 and the shoulder 38 of the displacement member 33. The bores 44 receive rods (not shown) which assist the user in rotating the knob 40 by providing additional leverage. The rods are releasably inserted in any selected one or more of the bores as desired during a surgical procedure. This helps the surgeon in attaching or releasing the implant to be described.

In operation of the displacement member 33, rotation of the knob 40 axially displaces the stud 34 in the shank portion 24 along the axis 30, FIG. 2. This moves the shoulder 38, FIG. 7 against the shank portion 22 along the axis 30. If the member is displaced toward the shank portion 22, the shoulder 38 will spread the shank portions 22 and 24 apart widening the gap 23. The shank portions bend relative to each other due to flexure of the material at their junction and/or also along the length of the shaft portions 22 and 24. The location of the flexure depends upon the thickness of the shaft portions 22 and 24. Flexure also may occur at the junction between the two shaft portions. This flexure is resilient so that any bending of the shaft portions results in a bias force tending to return the shaft portions to their quiescent position. This bias force will not cause the shaft portions to return to their quiescent position by itself due to the presence of the displacement member 33. The displacement member via its knob 40 must be rotated to do so. The displacement member 33 actively opens and closes the two shaft portions 22 and 24. In the closing position, the knob 40, when displaced toward portion 24, forces the captured flexed portion 22 to its quiescent position.

Displacement of the displacement member 33 toward shaft portion 24 moves the boss 48 abutting the shaft portion 22 in recess 32 toward the shaft portion 24 and thus displaces the shaft portion 22 also toward shaft portion 24 closing the gap 23.

A stop member 55, FIG. 8, comprises a shank 57 and a head 59. The shank 57 is threaded at threads 61 and is smooth at portion 63. The threads of the shank 57 are attached to mating threads 57', FIG. 9, in the shaft portion 24 and the head 59 is received in recess 65 in the shank portion 22. The shank portion 63 is received in a mating bore 67 in the shaft portion 22.

In operation of the stop member 55, the member 55 is threaded into the shank portion 24 a distance so that the head 59 is spaced from the bottom of the recess 65. The shank portions 22 and 24 can spread apart a distance until the head abuts the bottom wall of the recess 65. This limits the motion of the shaft portions and the amount they can spread apart. This prevents the shaft portions from being spread apart too great a distance which may be undesirable in certain implementations, conditions or uses of the tool 10.

A one piece integral extension 50 extends from shaft portion 22 and an extension 52 extends from shaft portion 24 in the distal direction to the right in FIGS. 1–3. The extensions are identical mirror images of each other. The extensions each have a rounded tip 54, FIG. 3, and have a width w smaller than the diameter of the shaft 12, and approximately one third that diameter, for example about 0.2 inches in this embodiment as compared to a shaft diameter of about 0.625 inches. The extensions 50 and 52 may form a gap g, FIG. 9, therebetween of about 0.33 inches in this embodiment. The extensions 50 and 52 are flat relatively thin elements, e.g., about 0.07 inches thick.

The extensions 50 and 52 each have a shoulder 56 approximately two thirds of the distance from the tip 54. The extensions 50 and 52 each extend from a distal end of the corresponding shank portion 22, 24, respectively. The distal end of the shank portions terminate in an implant impact surface 58, FIGS. 2 and 9. Each shank portion 22 and 24 has an implant impact surface 58 which abuts a received implant 60, FIG. 9. The impact surfaces 58 are coplanar with shoulders 56 of the extensions 50 and 52. The impact surfaces are defined by the end surface of a square in transverse section element 62, FIG. 9, at the end of each shaft portion 22 and 24. The shaft portions 22 and 24 taper to a thinner section at elements 62 from their diametrical dimensions as seen in the figures. The extensions 50 and 52 receive the implant 60 therebetween. The inner surfaces of the extensions are grooved in the axial direction of axis 13. The grooves are triangular in section and may be about 0.010 inches deep to grip the implant 60.

In FIGS. 10–13, implant 60 is formed of cortical bone and is described more fully in the aforementioned copending applications noted in the introductory portion and incorporated by reference herein. The implant 60 has a top surface 64 and a bottom surface 66. These surfaces have serrations in the form of repetitive identical ridges or saw teeth 68. The saw teeth 68 have a pitch which is determined for a given implant configuration. The surfaces 64 and 66 are inclined relative to the implant longitudinal axis 70 with a wider anterior end 72 and a narrower posterior end 74. End 72 is inserted first between the adjacent vertebra in the posterior approach. Surfaces 64 and 66 converge at posterior end 74 to height f in the range of about 7 to 13 mm from anterior height d in the range of about 9 to 15 mm at anterior end 74 in one embodiment.

In FIG. 11, the implant 60 has a curved semi-circular recess 76 in the body 78 of the of the implant. The recess 76 may be formed in part from the intramedullary canal in a long bone, and the recess may be machined to the desired shape. The implant is formed from the diaphysis or metaphysis of a long bone. The cortical ring is secured within a holding fixture and the sidewalls of the cortical ring are machined to provide the implant with the desired shape. The intramedullary canal may form the recess 76 which extends for the height d in communication with surfaces 64 and 66 on one side of the implant. The implant is formed from human or animal bone such as the fibula, radius, ulna, humerus, tibia or femur. Reference is made to the aforementioned copending application Ser. No. 09/328,242 incorporated by reference herein in its entirety for more detail in regard to the implant 60 and its manufacture. The implant 60 longitudinal axis 70 extends along the length of its body 78.

The implant 60 has two spaced surfaces 80 and 82 separated by the recess 76. The surfaces 80 and 82 are flat and coplanar. Surface 80 has a face dimension a such that at least two full ridges of the teeth 68 span the dimension a. Dimension b also is of a minimum length so that at least two full ridges of the teeth 68 span this dimension as well. Dimension h is about 8.5 mm in this embodiment. The length dimension L' is about 20 to about 23 mm. These dimensions are given by way of example, as other dimensions may be used according to a given implementation and procedure being performed. The processing of the bone including demineralization, treatment with bone growth enhancing factors or other appropriate processes is discussed in more detail in the aforementioned copending application.

In operation, the implant 60 is inserted between the extensions 50 and 52, FIG. 9, in the quiescent state of the extensions. The surgeon then turns the knob 40, FIG. 2, to tighten the extensions against the implant and grip the implant for spinal insertion in the disc space previously prepared in a known manner. The implant 60, in this embodiment, is shorter than the extensions which extend beyond the implant as shown in FIG. 9, the extensions 50 and 52 having a length greater than that of this implant. However, the lengths of the extensions 50 and 52 are such that at least one of them covers at least a portion of the surface 82 of an implant. Implants have different lengths in a range. The same insertion tool 10 is used to insert such implants. While in some cases the extensions may be longer than the implant, in other cases the extensions may be shorter. Thus regardless the implant length being used with the tool 10, at least a portion of the surface 82 of the shortest implant in the range will overly the corresponding extension. In this position, the implant abuts the impact surfaces 58 of the element 62 of the shaft portions 22 and 24. The member grip 20 at the proximal end of the shaft 20 is then impacted to drive the extensions 50 and 52 into the disc space. The surfaces 58 impact the implant abutting therewith. It should be understood that while each shaft portion 22 and 24 is shown with an impact element 62 and an impact surface 58, in some embodiments, only one such impact element 62 and corresponding surface need be provided. As shown in FIG. 9, the implant 60 in this embodiment abuts only one impact element 62' surface 58.

When it is time to remove the tool 10, the knob is reversed to open the extensions spreading them apart. This releases the implant. To avoid overly opening the extensions, the stop member 55 limits the spread apart distance to a reasonable clearance with the implant. The tool 10 is then retracted leaving the implant in place in the patient. The distance between the extensions 50 and 52 is nominally set at the same width h of the implant so the implant 60 is closely received in the gap g, FIG. 9, between the extensions. The extensions thus are closed further slightly to grip the implant.

In FIG. 14a, tool 86 comprises bifurcated shaft portions 88 and 90. Planar extension 92 extends from portion 88 and extension 94 extends from portion 90. Extension 92 has a thin planar section 92' and extension 94 has a thin planar section 94', which sections grip an implant therebetween. Extension 92 section 92' extends in the proximal direction 96 forming a recess 98.

Extension 94 extends from impact element 100 having an implant impact wall 102 normal to the extension 94. Wall 102 engages the end 74 of the implant 60, FIG. 11, for impacting the implant during spinal insertion of the implant.

In FIG. 14b, tool 104 has extensions 106 and 108. Impact element 110 is attached to shaft portion 112. Element 110 fits in recess 114 of shaft portion 116. Element 110 has a curvilinear wall 118 for mating engagement with an implant curved end wall (not shown).

It will occur to one of ordinary skill that various modifications may be made to the disclosed embodiments. For example while the displacement member is threaded, ramped cam devices such as mating bayonet type fittings, with or without a detent arrangement to provide incremental displacements, might also be employed to displace the shaft portions relative to each other. In a further alternative, a projection, with a detent or threaded engaging member attached, extending from one shaft portion may axially slidably engage a cam ramp in the other shaft portion so that axial displacement of the projection displaces the shaft portions relative to each other. It is intended that the scope of the invention is as defined in the appended claims.

What is claimed is:

1. An implant insertion tool comprising:
   an elongated shaft having a longitudinal axis and proximal and distal ends, the shaft having a bifurcated distal end forming first and second shaft portions arranged to flex toward and away from each other in a direction generally normal to the axis;
   a handle at the proximal shaft end;
   an implant gripping extension extending from each shaft portion in a distal direction for gripping an implant therebetween;
   a displacement member attached to the shaft portions for forcibly displacing the first and second portions relative to each other in the generally normal directions toward and away from each other, and the normal quiescent position of the extensions is arranged to receive the implant therebetween such that rotation of a knob cooperating with the displacement member closes the spacing between the extensions to grip the implant; and
   a stop member secured to said portions for limiting the maximum distance said shaft portions and extensions can separate.

2. The tool of claim 1 wherein the displacement member comprises a threaded stud, a smooth surface circular cylindrical shank attached to the stud and a knob attached to the shank distal the stud, the shank for rotatable attachment to the first shaft portion and the stud for threaded engagement with the second shaft portion, the shank, knob and stud being dimensioned to capture the second portion between the stud and the knob.

3. The tool of claim 2 wherein the stud has a diameter greater than that of the shank.

4. The tool of claim 1 wherein the stop member comprises a shank and a head attached to the shank, the end of the shank distal the head being threaded to one of said shaft first and second portions and the head engaged with the other of said shaft first and second portions, the head being larger than the shank for capturing the other of said shaft first and second portions thereto.

5. The tool of claim 1 wherein the displacement member comprises a threaded stud attached to the first shaft portion, a shank attached to and passing through the second shaft portion and a knob attached to the shank, the knob, shank and stud being arranged to capture the second member to the shank.

6. An implant insertion tool comprising:
   an elongated shaft having a longitudinal axis and proximal and distal ends, the shaft having a bifurcated distal end forming first and second shaft portions arranged to flex toward and away from each other in a direction generally normal to the axis;
   a handle at the proximal shaft end;
   an implant gripping extension extending from each said shaft portion in a distal direction for gripping an implant therebetween;
   a displacement member comprising a threaded stud attached to the first shaft portion, a shank attached to the second shaft portion and a knob arranged with the stud for capturing the second shaft portion between the stud and knob, the member for displacing the first and second portions apart and together in said generally normal directions toward and away from each other in response to rotation of the knob and stud; and
   a stop member secured to said portions capturing one of said first and second portions thereto for limiting the maximum distance said shaft portions and extensions can separate.

7. An implant insertion tool comprising:
   an elongated shaft having a longitudinal axis and proximal and distal ends, the shaft having a bifurcated distal end forming first and second shaft portions arranged to flex toward and away from each other in a direction generally normal to the axis;
   a handle at the proximal shaft end;
   an implant gripping extension extending from each the shaft portion in a distal direction for gripping an implant therebetween; and
   a displacement member attached to the shaft portions for displacing the first and second shaft portions relative to each other in the generally normal direction toward and away from each other, the displacement member comprising movable displacement means having first and second positions for forcing the shaft portions apart in the first position for receiving and releasing the implant and for forcing the shaft portions together to an implant gripping state in the second position.

8. The tool of claim 7 wherein the displacement member includes a threaded stud for engagement with one of said shank portions and a second shank portion attached to the stud for movably engaging the other of said shank portions and including a knob for rotating the stud and shank portion to place the stud, shank and knob in the first and second positions.

9. The tool of claim 7 further including a stop member coupled to the shaft portions for limiting the distance the shaft portions can be separated in the first position.

10. An implant insertion tool comprising:

an elongated shaft having a longitudinal axis and proximal and distal ends, the shaft having a bifurcated distal end forming first and second shaft portions arranged to flex toward and away from each other in a direction generally normal to the axis;

a handle at the proximal shaft end;

an implant gripping extension extending from each the shaft portion in a distal direction for gripping an implant therebetween;

a displacement member attached to the shaft portions for displacing the first and second portions relative to each other in the generally normal directions toward and away from each other, the displacement member comprises a threaded stud, a smooth surface circular cylindrical shank attached to the stud and a knob attached to the shank distal the stud, the shank for rotatable attachment to the first shaft portion and the stud for threaded engagement with the second shaft portion, the shank, knob and stud being dimensioned to capture the second portion between the stud and the knob; and a stop member secured to said portions for limiting the maximum distance said shaft portions and extensions can separate.

11. An implant insertion tool comprising:

an elongated shaft having a longitudinal axis and proximal and distal ends, the shaft having a bifurcated distal end forming first and second shaft portions arranged to flex toward and away from each other in a direction generally normal to the axis;

a handle at the proximal shaft end;

an implant gripping extension extending from each the shaft portion in a distal direction for gripping an implant therebetween;

a displacement member attached to the shaft portions for displacing the first and second portions relative to each other in the generally normal directions toward and away from each other; and a stop member secured to said portions for limiting the maximum distance said shaft portions and extensions can separate, the stop member comprises a shank and a head attached to the shank, the end of the shank distal the head being threaded to one of said shaft first and second portions and the head engaged with the other of said shaft first and second portions, the head being larger than the shank for capturing the other of said shaft first and second portions thereto.

12. An implant insertion tool comprising:

an elongated shaft having a longitudinal axis and proximal and distal ends, the shaft having a bifurcated distal end forming first and second shaft portions arranged to flex toward and away from each other in a direction generally normal to the axis;

a handle at the proximal shaft end;

an implant gripping extension extending from each the shaft portion in a distal direction for gripping an implant therebetween;

a displacement member attached to the shaft portions for displacing the first and second portions relative to each other in the generally normal directions toward and away from each other, the displacement member comprises a threaded stud, a smooth surface circular cylindrical shank attached to the stud and a knob attached to the shank distal the stud, the shank for rotatable attachment to the first shaft portion and the stud for threaded engagement with the second shaft portion, the shank, knob and stud being dimensioned to capture the second portion between the stud and the knob where the stud has a diameter greater than that of the shank; and a stop member secured to said portions for limiting the maximum distance said shaft portions and extensions can separate.

13. An implant insertion tool comprising:

an elongated shaft having a longitudinal axis and proximal and distal ends, the shaft having a bifurcated distal end forming first and second shaft portions arranged to flex toward and away from each other in a direction generally normal to the axis;

a handle at the proximal shaft end;

an implant gripping extension extending from each the shaft portion in a distal direction for gripping an implant therebetween;

a displacement member attached to the shaft portions for displacing the first and second portions relative to each other in the generally normal directions toward and away from each other, the displacement member comprises a threaded stud attached to the first shaft portion, a shank attached to and passing through the second shaft portion and a knob attached to the shank, the knob, shank and stud being arranged to capture the second member to the shank; and a stop member secured to said portions for limiting the maximum distance said shaft portions and extensions can separate.

* * * * *

UNITED STATES PATENT AND TRADEMARK OFFICE
CERTIFICATE OF CORRECTION

PATENT NO. : 6,746,454 B2
DATED : June 8, 2004
INVENTOR(S) : John M. Winterbottom et al.

It is certified that error appears in the above-identified patent and that said Letters Patent is hereby corrected as shown below:

Column 2,
Line 34, change "brand" to -- branch --.
Line 45, change "the" to -- The --.

Column 4,
Line 17, after "medially" insert -- to --.

Column 6,
Lines 20-21, after "and" insert and change to read as follows: -- the ring is cut in half to form two C-shaped implants. The sidewalls of the cortical ring halves are --.

Column 9,
Line 46, before "displacing" insert -- forcibly --.

Signed and Sealed this

Twenty-third Day of November, 2004

JON W. DUDAS
*Director of the United States Patent and Trademark Office*